April 22, 1969 F. W. ANDERSON Plant Pat. 2,880
APRICOT TREE
Filed Sept. 11, 1967
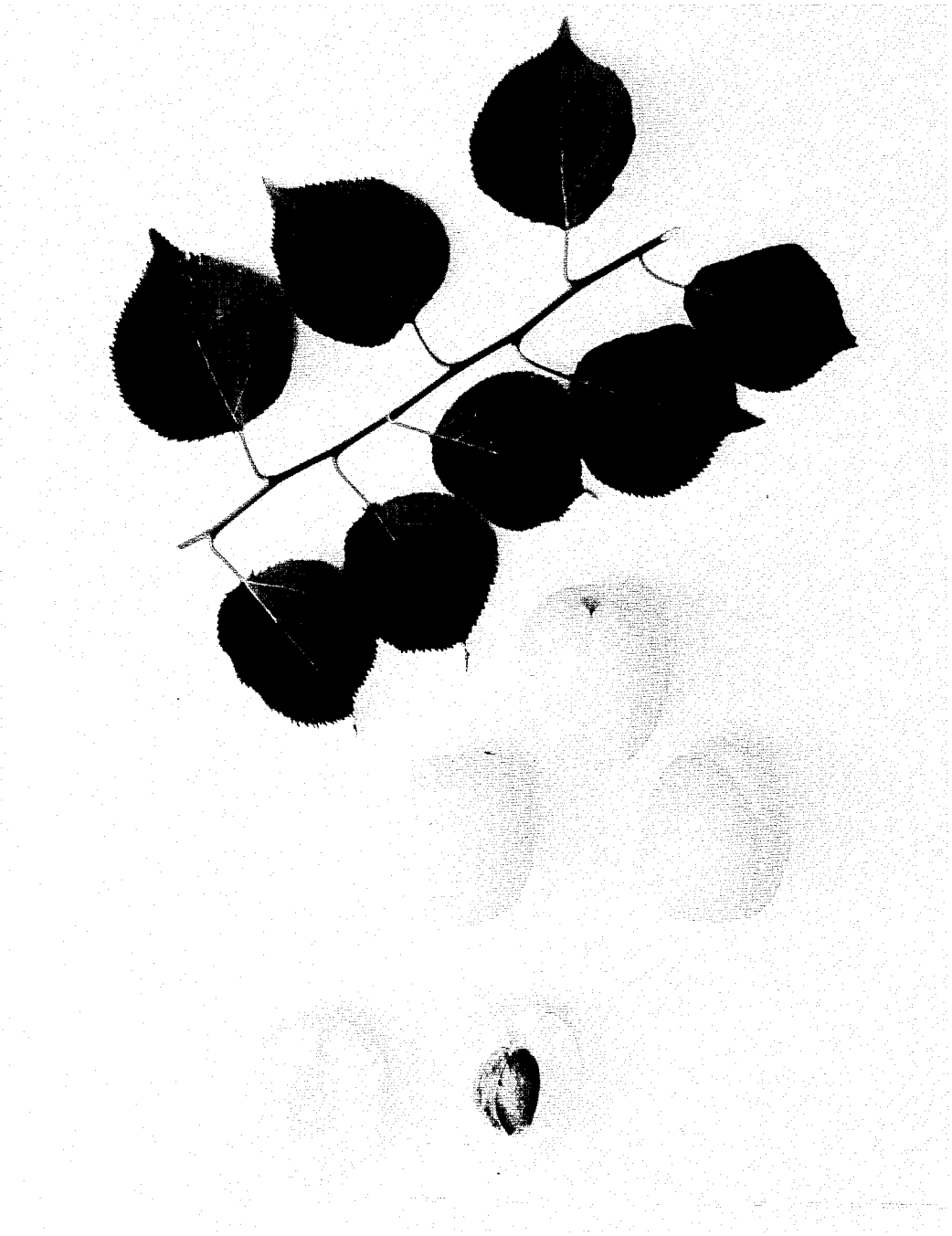
INVENTOR
*Frederic W. Anderson*
BY
*Webster & Webster*
ATTORNEYS United States Patent Office Plant Pat. 2,880
Patented Apr. 22, 1969

2,880

APRICOT TREE

Frederic W. Anderson, Merced, Calif., assignor to Reedley Nursery, Inc., Reedley, Calif., a corporation Filed Sept. 11, 1967, Ser. No. 667,013
U.S. Cl. Plt.—39 1 Claim

ABSTRACT OF THE DISCLOSURE

A cultivar of apricot tree which is a regular and very productive bearer of an unusually early ripening, freestone fruit having commercially desirable characteristics.

*Background of the variety*

Over a substantial number of years I have engaged in an extensive and continuing plant breeding program at my experimental nursery and orchard located near Le Grand, Merced County, Calif.; one purpose of such program being to provide improved varieties of fruit trees. The present variety of apricot tree resulted from my endeavors in the course of such plant breeding program.

*Origin of the variety*

The herein claimed variety of apricot tree was originated by me, in the aforesaid experimental nursery and orchard, as a second generation seedling of "Perfection" (unpatented). Several thousand seedlings of the same origin were grown under conditions of close observation, and the instant variety is one therefrom which evidenced distinctive characteristics which made it advantageous for commercial growing. The variety was, therefore, selected by me for asexual reproduction.

*Asexual reproduction of the variety*

I accomplished asexual reproduction of the present variety of apricot tree by multiple budding on mature trees in my aforementioned orchard; such reproduction having run true to the original tree in all respects.

*Summary of the variety*

The present variety of apricot tree is new and distinct by virtue of the following characteristics:

The tree is a regular and very productive bearer of uniform size, yellow flesh, freestone fruit having an unusually early ripening period and which, on the approximate average, is ten days before "Pomo" (United States Plant Patent No. 2,192), two weeks before "Madesto" (United States Plant Patent No. 2,515), and three weeks before "Royal-Blenheim" (unpatented).

The yellow flesh of the fruit is much firmer than that of any apricot variety now available, and such firmness of flesh gives substantial promise that the fruit can be harvested, and otherwise handled, mechanically. Also, such firmness of flesh permits the fruit to be shipped long distances, and marketed over a comparatively long period of time without loss of attractive appearance. Further, the fruit, by reason of its firmness of flesh, processes—as by canning or drying—in an excellent manner.

*Brief description of the drawing*

The drawing is an illustration, by photographic reproduction in color, of fruit of the variety, together with a twig with leaves; the view including one fruit cut in half in the suture plane, with the stone remaining in one half.

*Description of the variety*

The botanical details of this new and distinct variety of apricot tree—with color definitions (except those in common color terms) referenced to Maerz and Paul Dictionary of Color—are as follows:

Tree:
- *Size.*—Medium.
- *Vigor.*—Medium.
- *Growth.*—Spreading.
- *Density.*—Open.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Red to green.
- *Lenticels.*—Number—medium. Size—medium.

Leaves:
- *Size.*—Large to medium. Average length—3". Average width—2⅞".
- *Form.*—Cordate—acutely pointed.
- *Thickness.*—Medium.
- *Texture.*—Smooth.
- *Margin.*—Finely serrate.
- *Petiole.*—Medium length; medium thickness to slender.
- *Glands.*—Average number.—4. Alternate; small; globose; positioned usually 2 on petiole and 2 on leaf margin near base.
- *Color.*—Top side—Medium Green (22–L–9). Underside—Lighter Green (21–L–8).

Flower buds:
- *Size.*—Small.
- *Length.*—Medium.
- *Form.*—Conic.

Flowers:
- *Blooming period.*—About one week before Royal-Blenheim.
- *Size.*—Medium.
- *Color.*—White petals, reddish sepals.

Fruit:
- *Maturity when described.*—Eating ripe—June 10, 1967.
- *Date of first picking.*—May 30, 1967.
- *Date of last picking.*—June 20, 1967.
- *Size.*—Uniform; medium. Average diameter axially—2⅜". Average transversely insuture plane—2".
- *Form.*—Unsymmetrical; oblong, compressed laterally.
- *Suture.*—Distinct; extends from base to apex.
- *Cavity.*—Elongated in suture plane with suture showing on one side; very shallow. Markings—none.
- *Apex.*—Depressed.
- *Pistill point.*—Absent.

Skin:
- *Thickness.*—Medium.
- *Texture.*—Medium.
- *Tenacity.*—Tenacious to flesh.
- *Tendency to crack.*—None noted.
- *Color.*—Normal Apricot Yellow (10–L–5) blushed and slightly mottled with Red (4–K–10) on sunny side.

Flesh:
- *Texture.*—Very firm; tough; meaty.
- *Fibers.*—Few; tender.
- *Ripens.*—Evenly.
- *Flavor.*—Subacid; delicate.
- *Eating quality.*—Good.
- *Color.*—Normal Apricot Yellow (9–L–7). Surface of pit cavity—yellow with yellow fibers.

Stone:

*Type.*—Free.

*Size.* — Medium. Average length — 1″. Average breadth—¾″. Average thickness—½″.

*Form.*—Oblong.

*Hilum.*—Narrow.

*Apex.*—Rounded.

*Sides.*—Equal.

*Ridges.*—One either side—stone smooth.

*Ventral edge.*—Thin, with wing throughout.

*Dorsal edge.*—Full, without groove.

*Tendency to split.*—None noted.

*Color.*—Brown (8–H–8).

Use: Market; canning; drying.

Keeping quality: Excellent—long shelf life.

Shipping quality: Excellent.

The apricot tree and its fruit herein described may vary in slight detail due to climatic and soil conditions under which the variety may be grown; the present description being of the variety as grown in the Central Valley of California, and wherein in 1967 all fruit ripened over two weeks later than normal.

I claim:

1. A new and distinct variety of apricot tree, substantially as illustrated and described, which is a regular and very productive bearer of freestone fruit characterized by very firm, yellow flesh, and by a ripening period which on the approximate average is ten days before Pomo, two weeks before Modesto, and three weeks before Royal-Blenheim.

No references cited.

ROBERT E. BAGWILL, *Primary Examiner.*